United States Patent [19]

Hill

[11] 4,188,397

[45] Feb. 12, 1980

[54] 2,2-ALKYLDIYLBIS(THIO)BIS-(IMIDAZOLES)

[75] Inventor: David T. Hill, North Wales, Pa.

[73] Assignee: SmithKline Corporation, Philadelphia, Pa.

[21] Appl. No.: 944,672

[22] Filed: Sep. 22, 1978

[51] Int. Cl.$^2$ .................. A61K 31/415; C07D 233/84
[52] U.S. Cl. .................. 424/273 R; 548/322; 548/336
[58] Field of Search .................. 548/336; 424/273 R

[56] References Cited

U.S. PATENT DOCUMENTS

| 3,070,599 | 12/1962 | Hendry et al. | 548/336 |
| 3,086,018 | 4/1963 | Hardman | 548/336 |

FOREIGN PATENT DOCUMENTS 960279  3/1957  Fed. Rep. of Germany .......... 548/336

OTHER PUBLICATIONS

Gupta et al., Indian J. Chem., 1978, vol. 16B, pp. 329–331.
Johnson et al., J. Amer. Chem. Soc., 1942, vol. 64, pp. 2706–2708.
Ogura et al., Chem. Pharm. Bull., 1968, vol. 16(11), pp. 2167, 2168, 2170 & 2171.
Searle, J. Appl. Chem., (London), 1955, vol. 5, pp. 313–316.

*Primary Examiner*—Natalie Trousof
*Attorney, Agent, or Firm*—Janice E. Williams; William H. Edgerton; Alan D. Lourie

[57] ABSTRACT

New 2,2'-alkyldiylbis(thio)bis(imidazoles) having substituted phenyl groups in the 4- and 5- positions of the imidazole rings are disclosed. These compounds regulate cell-mediated immunity and/or have anti-arthritic activity and are useful to relieve inflammation, for example in the treatment of rheumatoid arthritis.

17 Claims, No Drawings

2,2-ALKYLDIYLBIS(THIO)BIS(IMIDAZOLES)

This invention relates to new 2,2'-alkyldiylbis(thio)-bis(imidazoles) having a substituted phenyl group in the 4- and 5- positions of the imidazole rings. These compounds regulate cell-mediated immunity and/or have anti-arthritic activity and are useful to relieve inflammation, for example in the treatment of rheumatoid arthritis.

The compounds of this invention are represented by the following structural formula:

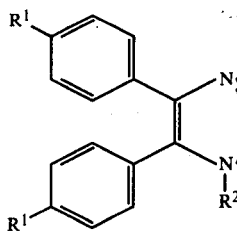 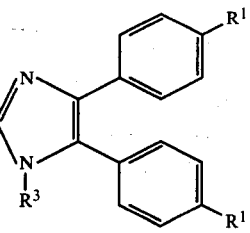

FORMULA I in which:

$R^1$ is methoxy, methylthio, trifluoromethyl, chloro, fluoro, bromo or methylenedioxy when taken with an adjacent position on the phenyl ring;

$R^2$ and $R^3$ are both hydrogen or one is hydrogen and the other is methyl;

n is 0, 1 or 2; and

X is selected from the group consisting of —(CH$_2$-)$_m$— where m is 0 to 4 provided that m is not 0 when $R^1$ is chloro,

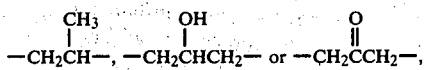

or a non-toxic, pharmaceutically acceptable salt thereof.

A selected group of compounds of this invention are those represented by Formula I where $R^1$ is methoxy or fluoro.

Another group of compounds of this invention are those represented by Formula I where $R^1$ is methoxy or fluoro, n is 0 and X is —(CH$_2$)$_m$— where m is 0, 1 or 2,

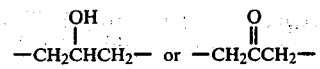

Some examples of the compounds of this invention are the following:

2,2'-[1,2-ethanediylbis(thio)]bis[4,5-bis(4-fluorophenyl)-1H-imidazole]

2,2'-thiobis[4,5-bis(4-fluorophenyl-1H-imidazole]

2,2'-[methanediylbis(thio)]bis(sulfoxy)]bis[4,5-bis(4-fluorophenyl)-1H-imidazole]

2,2'-[1,2-ethanediylbis(sulfoxy)]bis[4,5-bis(4-fluorophenyl)-1H-imidazole]

4,5-bis(4-fluorophenyl)-2-[2-(4,5-bis(4-fluorophenyl)-1H-2-imidazolylthio)ethylthio]-1-methylimidazole 2,2'-[1,3-propan-2-oldiylbis(thio)]bis[4,5-bis(4-fluorophenyl)-1H-imidazole]

2,2'-[1,3-propan-2-onediylbis(thio)bis[4,5-fluorophenyl)-1H-imidazole].

Some bis-imidazole compounds are known. Johnson et al., *J. Am. Chem. Soc.* 64:2706 (1942) disclose the compounds 2,2'-thiobis(1H-imidazole) and 2,2'-thiobis(4-bis(methyl)-1H-imidazole]. German Patent No. 960,279 discloses 2,2'-thiobis[4,5-bis(phenyl)-1H-imidazole], bis(1-methyl-2-1H-imidazolyl)disulfide and bis(1-phenyl-2-imidazolyl)disulfide. The compound 2,2'-[methanediylbis(thio)-1H-imidazole] is described by Searle, *J. Appl. Chem.* (London) 5:313 (1955) and Ogura et al., *Chem. Pharm. Bull.* 16(11):2167 (1968) report the synthesis of 1,2-bis(2-benzimidazolylthio)ethane. The substituted bis-imidazole compounds of this invention are not believed to be known to the art.

The compounds of this invention where $R^2$ and $R^3$ are both hydrogen, n is 0 and m is 1 to 4 are prepared according to the following reaction scheme:

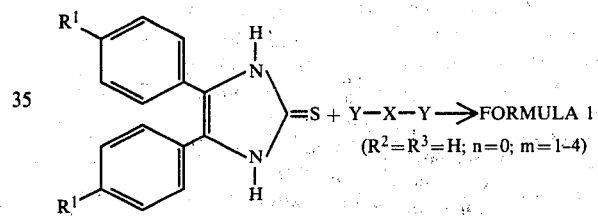

where $R^1$ and X are defined as above, except that m is not 0, and Y is halo, preferably chloro or bromo.

According to the above scheme an appropriately substituted imidazole-2-thione is reacted with a dihaloalkane such as 1,2-dibromoethane, a dihalopropanol or a dihalopropanone to give the compounds of Formula I. The reaction is preferably carried out in a polar organic solvent such as methanol, ethanol, dioxane or N,N-dimethylformamide at a temperature of from about ambient temperature to the boiling point of the solvent. Isolation of the product employing standard techniques affords a compound of Formula I as a dihydrohalide salt which may be converted to the free base by known procedures, for example by reaction with a base.

When m is 0 (disulfide linkage), the compounds of Formula I where $R^2$ and $R^3$ are hydrogen and n is 0 are preferably prepared by reaction of the correspondingly substituted imidazole-2-thione with iodine or an iodine-carrier such as 1,2-diiodotetrafluoroethylene in the presence of a base such as sodium ethoxide.

The compounds of Formula I where one of $R^2$ and $R^3$ is methyl are prepared from the corresponding compounds of Formula I where $R^2$ and $R^3$ are both hydrogen by treatment with sodium hydride followed by the addition of methyl iodide.

When n is 1 (sulfoxide compounds), the compounds of Formula I are prepared by treatment of the corresponding compounds where n is 0 with m-chloroperbenzoic acid according to standard procedures.

The compounds of Formula I where n is 2 (sulfone compounds) are prepared by oxidation of the corresponding compounds where n is 0 with hydrogen peroxide, also according to standard methods.

The thione starting materials are prepared from the appropriately substituted benzoins, which are known to the art or prepared by known methods, by reaction of the benzoin with thiourea in a solvent such as N,N-dimethylformamide or hexanol.

The pharmaceutically acceptable acid addition salts of the compounds of the Formula I are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The compounds of this invention are useful as anti-arthritic agents and as regulators of cell-mediated immunity.

The ability to regulate cell-mediated immunity is determined by the oxazolone-induced contact sensitivity test procedure in which changes in mouse paw edema produced by administration of the test compound are measured. This test procedure is described by Griswold et al., *Cellular Immunology* 11:198 (1974) and Griswold et al., *Inflammation* 2(4):277 (1977). The implication of cell-mediated immune reactivity in rheumatoid arthritis is described by Basch et al., *J. Rheumatology* 4:377 (1977). Many of the compounds of this invention enhance the oxazolone-induced response at doses of from about 12.5–100 mg/kg, orally. Specific examples of this activity exhibited by certain compounds of this invention appear in Table 1.

TABLE 1

| OXAZOLONE INDUCED CONTACT SENSITIVITY | | |
|---|---|---|
| COMPOUND | Dose (mg/kg) (based on free base) | % Increase Over Controls of Mouse Paw Edema Volume |
| 2,2'-[1,2-Ethanediylbis(thio)]bis[4,5-bis(4-fluorophenyl)-1H-imidazole] dihydrobromide | 25 | 64 |
| 2,2'-Thiobis[4,5-bis(4-fluorophenyl)-1H-imidazole] | 25 | 134 |
| 2,2'-[Methanediylbis(thio)]bis[4,5-bis(4-fluorophenyl)-1H-imidazole] dihydrobromide | 25 | 40 |
| 2,2'-[1,2-Ethanediylbis(sulfoxy)]bis[4,5-bis(4-fluorophenyl)-1H-imidazole] dihydrochloride | 25 | 62 |
| 4,5-Bis(4-fluorophenyl)-2-[2-(4,5-bis(4-fluorophenyl)-1H-2-imidazolylthio)ethylthio]-1-methylimidazole dihydrobromide | 25 | 52 |
| 2,2'-[1,3-Propan-2-oldiylbis(thio)]bis[4,5-bis(4-fluorophenyl)-1H-imidazole] dihydrobromide | 25 | 68 |
| 2,2'-[1,3-Propan-2-onediylbis(thio)]bis[4,5-bis(4-fluorophenyl)-1H-imidazole] dihydrochloride | 25 | 72 |

The anti-arthritic activity of the compounds of this invention is demonstrated by their ability to inhibit adjuvant induced polyarthritis in rats as measured by reduction of rat paw edema at daily doses of about 12.5–100 mg/kg orally. In this test procedure, adjuvant arthritis is produced in rats by a single intradermal injection of 0.75 mg. of *Mycobacterium butyricum* suspended in white paraffin oil into the left hindpaw footpad. The injected paw becomes inflammed (increased volume) and reaches maximum size within three to five days (primary lesion). The animals exhibit a decrease in body weight gain during the initial period. The adjuvant arthristis (secondary lesion) occurs after approximately ten days and is characterized by inflammation of the non-injected right hind leg, decrease in body weight and further increase in the volume of the injected left hind leg. Test compounds are administered daily beginning on the day of the adjuvant injection for seventeen days thereafter exclusive of days 4, 5, 11 and 12. Anti-inflammatory activity is shown by a decrease in volume of the inflammed leg and antiarthristic activity is shown by the ability to protect the animals against development of both primary and secondary lesions of adjuvant arthritis. Specific examples of this activity exhibited by certain compounds of this invention appear in Table 2.

TABLE 2

| ADJUVANT INDUCED ARTHRITIS | | | | |
|---|---|---|---|---|
| | | Injected (left) Hindleg Volume (cc.) | | Uninjected (right) Hindleg Volume (cc.) |
| COMPOUND | Dose (mg/kg/day) | Day 3 | Day 16 | Day 16 |
| 2,2'-[1,2-Ethanediylbis(thio)]bis[4,5-bis(4-fluorophenyl)-1H-imidazole] dihydrobromide | 50 | −18 | −30 | −30 |
| 2,2'-Thiobis[4,5-bis(4-fluorophenyl)-1H-imidazole] | 50 | −18 | −17 | −20 |
| 2,2'-[Methanediylbis(thio)]bis(4,5-bis(4-fluorophenyl)-1H-imidazole] dihydrobromide | 50 | −24 | −34 | −43 |
| 2,2'-[1,2-Ethanediylbis(sulfoxy)]bis[4,5-bis(4-fluorophenyl)-1H-imidazole] dihydrochloride | 50 | −27 | −31 | NS* |
| 4,5-Bis(4-fluorophenyl)-2-[2-(4,5-bis(4-fluorophenyl)-1H-2-imidazolylthio)ethylthio]-1-methylimidazole dihydrobromide | 50 | −19 | −16 | NS* |
| 2,2'-[1,3-Propan-2-oldiylbis(thio)]bis[4,5-bis(4-fluorophenyl)-1H-imidazole] dihydrobromide | 50 | −34 | −45 | −30 |
| 2,2'-[1,3-Propan-2-onediylbis(thio)]bis[4,5-bis(-4-fluoro- | | | | |

TABLE 2-continued

| | | ADJUVANT INDUCED ARTHRITIS | | |
|---|---|---|---|---|
| | | Injected (left) Hindleg Volume (cc.) | | Uninjected (right) Hindleg Volume (cc.) |
| COMPOUND | Dose (mg/kg/day) | Day 3 | Day 16 | Day 16 |
| phenyl)-1H-imidazole] dihydrochloride | 50 | −26 | −33 | −31 |
| Prednisolone | 20 | −35 | −43 | −58 |

*NS = not significant

A selected group of the compounds of this invention, namely those listed above as examples of the invention, exhibit both regulation of cell-mediated immunity and anti-arthritic activity.

Because of the pharmacological profile of the compounds of this invention, it is expected that they would be useful as anti-inflammatory agents in man. Some of the compounds are also useful as anti-arthritic agents.

The compounds of this invention are administered in comventional dosage forms prepared by combining a compound of Formula I or a salt thereof in an amount sufficient to produce activity with a standard pharmaceutical carrier according to conventional procedures. These procedures may involve mixing, granulating and compressing or dissolving the ingredients as appropriate to the desired preparation. The resulting pharmaceutical compositions are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include a time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampule or a nonaqueous liquid suspension.

To obtain a stable water soluble dose form, a pharmacuetically acceptable acid addition salt, preferably hydrochloride or sulfate, of a compound of Formula I is dissolved in an aqueous solution of an organic or inorganic acid, such as a 0.3 M solution of succinic acid or, preferably, citric acid. In addition to sulfate and hydrochloride, methanesulfonate, phosphate and hydrobromide are exemplary of other water soluble salt.

Preferably, each dosage unit will contain the active ingredient in an amount of from about 25 mg to about 200 mg.

The method of regulating cell-mediated immunity and/or producing anti-arthritic activity by administering internally to an animal a compound of Formula I is also an object of this invention. The compound is administered in amounts sufficient to produce the activity desired. The route of administration may be orally or parenterally. The daily dosage regimen will be preferably from about 75 mg to about 600 mg. When the method is carried out as described above, the desired activity is produced.

One skilled in the art will recognize that in determining the amounts of the active ingredient in the claimed compositions and used in the claimed methods, the activity of the chemical ingredient as well as the size of the host animal must be considered.

The following examples do not limit the disclosure but are illustrative of the invention. All temperatures are in degrees Centigrade (°C.) unless otherwise noted.

EXAMPLE 1

2,2'-[1,2-Ethanediylbis(thio)]bis[4,5-bis(4-bromophenyl)-1H-imidazole]

A mixture of 4,4'-dibromobenzoin (25 g, 0.068 mol) and thiourea (10.3 g, 0.14 mol) in hexanol (200 ml) was refluxed with azeotropic distillation of water for three hours. The solution was then cooled and ethanol (300 ml) was added. The mixture was further cooled and the small needles which formed were collected and washed with cold ethanol then ether and dried. Recrystallization of the product from ethyl acetate gave 4,5-bis-(4-bromophenyl)-1H-imidazole-2-thione, m.p. 288°.

A mixture of 4,5-bis(4-bromophenyl)-1H-imidazole-2-thione (10 g, 0.024 mol) and 1,2-dibromoethane (2.3 g. 0.012 mol) in ethanol (100 ml) was heated at reflux temperature for eleven hours and then cooled to ambient temperature. The resulting product was removed by filtration, washed with ether and recrystallized from methanol to give the title compound as its dihydrobromide salt, m.p. 244°-251°.

$C_{32}H_{22}Br_4N_4S_2$ 2 HBr Calculated: 38.13% C; 2.40% H; 5.56% N. Found: 37.94% C; 2.53% H; 5.52% N.

2,2'-[1,2-Ethanediylbis(thio)]bis[4,5-bis(4-bromophenyl)-1H-imidazole] dihydrobromide (ca. 65 g) was slurried with warm ethanol (150 ml) and 5% aqueous sodium carbonate (500 ml) was added. The mixture was filtered and the precipitate was washed with water then ethanol, air-dried and recrystallized to give the title compound.

EXAMPLE 2

2,2'-[1,2-Ethanediylbis(thio)]bis[4,5-bis(4-trifluoromethylphenyl)-1H-imidazole]

A solution of p-trifluoromethylbenzaldehyde (50 g, 0.24 mol), 3-ethyl-5-(2-hydroxyethyl)-4-methyl-1,3-thiazolium bromide (3.6 g, 0.014 mol) and triethylamine (8.8 g. 0.087 mol) in ethanol (200 ml) was refluxed 1.5 hours under an argon atmosphere. After cooling, the mixture was poured into water and extracted immediately into chloroform, taking precautions to exclude air as much as possible. The chloroform extracts were washed with 5% aqueous sodium bicarbonate solution and water and then dried (MgSO$_4$). Removal of the solvent at reduced pressure gave a nearly quantitative yield of crude 4,4'-di(trifluoromethyl)benzoin which was used without further purification.

A mixture of 4,4'-di(trifluoromethyl)benzoin (50 g, 0.15 mol) and thiourea (15.2 g, 0.2 mol) in dimethylformamide (350 ml) was refluxed under argon for three hours. The cooled solution was poured into 1 liter of water and the resulting solid was collected, washed with water, air-dried and recrystallized from ethanol to give 4,5-bis-(4-trifluoromethylphenyl)-1H-imidazole-2-thione, m.p. 312°–315°.

A mixture of 4,5-bis(4-trifluoromethylphenyl)-1H-imidazole-2-thione (8 g, 0.02 mol) and 1,2-dibromoethane (2.2 g, 0.017 mol) in ethanol (100 ml) was refluxed overnight. The mixture was cooled and the precipitate was removed by filtration and recrystallized from ethanol to give the title compound as its dihydrobromide salt, m.p. 252°–254°.

$C_{36}H_{22}F_{12}N_4S_2.2$ HBr Calculated: 44.83% C: 2.51% H; 5.81% N; 16.57% Br. Found: 44.85% C; 2.68% H; 5.68% N; 16.37% Br.

2,2'-[1,2-Ethanediylbis(thio)]bis[4,5-bis(4-trifluoromethylphenyl)-1H-imidazole] dihydrobromide was converted to the title compound by the procedure described in Example 1.

EXAMPLE 3

2,2'-[1,2-Ethanediylbis(thio)]bis[4,5-bis(4-methoxyphenyl)1H-imidazole]

4,5-Bis(4-methoxyphenyl)-1H-imidazole-2-thione, m.p. 265°, was prepared by substitution of an equivalent amount of 4,4'-dimethoxybenzoin in either of the procedures for preparing imidazole thiones described in Examples 1 and 2.

A mixture of 4,5-bis(4-methoxyphenyl)-1H-imidazole-2-thione (31.2 g, 0.1 mol) and 1,2-dibromoethane 9.3 g, 0.05 mol) in ethanol (300 ml) was refluxed for four hours. After cooling, the solvent was removed at reduced pressure and the resulting solid was treated with ether and then filtered. The solid product was recrystallized several times from ethanol to give the title compound as its dihydrobromide salt (hydrate), m.p. 228°.

$C_{36}H_{34}N_4O_4S_2.2$ HBr.1.5 $H_2O$ Calculated: 51.44% C; 4.68% H; 6.67% N. Found: 51.37% C; 4.81% H; 6.52% N.

2,2'-[1,2-Ethanediylbis(thio)]bis[4,5-bis(4-methoxyphenyl)-1H-imidazole] dihydrobromide is converted to the title compound by the procedure described in Example 1.

EXAMPLE 4

2,2'-[1,2-Ethanediylbis(thio)]bis[4,5-bis(4-chlorophenyl)-1H-imidazole]

4,5-Bis(4-chlorophenyl)-1H-imidazole-2-thione was prepared by substitution of an equivalent amount of 4,4'-dichlorobenzoin in either of the procedures for preparing imidazole thiones described in Examples 1 and 2.

A mixture of 4,5-bis(4-chlorophenyl)-1H-imidazole-2-thione (20 g, 0.062 mol) and 1,2-dibromoethane (5.8 g, 0.031 mol) in ethanol (200 ml) was refluxed for 6.5 hours. The resulting solid product was removed by filtration and washed with ethanol and then ether. Recrystallization from methanol gave the title compound as its dihydrobromide salt (hydrate), m.p. 251°–252°.

$C_{32}H_{22}Cl_4N_4S_2.2$ HBr.2.5 $H_2O$ Calculated: 43.91% C; 3.11% H; 6.40% N; 7.40% S. Found: 43.81% C; 3.25% H; 6.36% N; 7.54% S.

2,2'-[1,2-Ethanediylbis(thio)]bis[4,5-bis(4-chlorophenyl)-1H-imidazole] dihydrobromide is converted to the title compound by the procedure described in Example 1.

EXAMPLE 5

2,2'-[1,2-Ethanediylbis(thio)]bis[4,5-bis(4-fluorophenyl)1H-imidazole]

4,5-Bis(4-fluorophenyl)-1H-imidazole-2-thione, m.p. 309°–311°, was prepared by substitution of an equivalent amount of 4,4'-difluorobenzoin in either of the procedures for preparing imidazole thiones described in Examples 1 and 2.

A mixture of 4,5-bis(4-fluorophenyl)-1H-imidazole-2-thione (15.2 g, 0.053 mol) and 1,2-dibromoethane (4.9 g, 0.026 mol) in dioxane (300 ml) was refluxed for 2.5 hours and then cooled. The resulting solid was removed by filtration, then washed with ether and recrystallized from ethanol-ether-dimethylformamide (35:60:5) to give the title compound as its dihydrobromide salt (hydrate), m.p. 302°–304°.

$C_{32}H_{22}F_4N_4S_2.2$ HBr.2 $H_2O$ Calculated: 48.01% C; 3.59% H; 7.00% N; 19.96% Br. Found: 48.24% C; 3.83% H; 6.77% N; 19.57% Br.

2,2'-[1,2-Ethanediylbis(thio)]bis[4,5-bis(4-fluorophenyl)-1H-imidazole] dihydrobromide was converted to the title compound by the procedure described in Example 1, m.p. 307°–310°.

$C_{32}H_{22}F_4N_4S_2$ Calculated: 63.77% C; 3.68% H; 9.30% N. Found: 63.37% C; 3.84% H; 9.12% N.

A solution 2,2'-[1,2-ethanediylbis(thio)]bis-[4,5-bis(4-fluorophenyl-1H-imidazole] dihydrobromide (10 g) in methanol (400 ml) was passed through a column of AG1-X10 analytical grade anion exchange resin, chloride form (200 g) to give, after removal of the solvent and recrystallization from methanol, the title compound as its dihydrochloride salt (hydrate), m.p. 190°–195° (dec.).

$C_{32}H_{22}F_4N_4S_2.2$ HCl.$H_2O$ Calculated: 55.41% C; 3.78% H; 8.07% N. Found: 54.95% C; 4.02% H; 8.05% N.

A mixture of 4,5-bis(4-fluorophenyl)-1H-imidazole-2-thione (10 g, 0.034 mol), 1,2-dichloroethane (1.7 g, 0.017 mol) in N,N-dimethylformamide (45 ml) was stirred for 24 hours at 80° and then cooled. The precipitate was harvested and recrystallized from methanol to give the trihydrate, m.p. 234°–236°.

$C_{32}H_{22}F_4N_4S_2$ 2 HCl 3 $H_2O$ Calculated: 52.68% C; 4.14% H; 7.68% N Found: 52.95% C; 3.79% H; 7.82% N

EXAMPLE 6

2,2'[1,3-Propanediylbis(thio)]bis[4,5-bis(4-fluorophenyl)1H-imidazole]

A mixture of 4,5-bis(4-fluorophenyl)-1H-imidazole-2-thione (8 g, 0.028 mol) and 1,3-dibromopropane (2.8 g, 0.014 mol) in dioxane (175 ml) was refluxed for 2.5 hours. After cooling, ether (300 ml) was added and the resulting white solid was collected by filtration, washed with ether and recrystallized from dioxane-ether to give the title compound as its dihydrobromide salt (hydrate), m.p. 176°–178°.

$C_{33}H_{24}F_4N_4S_2.2$ HBr.1.5 $H_2O$ Calculated: 49.20% C; 3.63% H; 6.96% N; 19.84% Br. Found: 49.38% C; 3.88% H; 6.70% N; 20.08% Br.

2,2'-[1,3-Propanediylbis(thio)]bis[4,5-bis(4-fluorophenyl)-1H-imidazole] dihydrobromide is converted to the title compound by the procedure described in Example 1.

EXAMPLE 7

2,2'-[1,4-Butanediylbis(thio)]bis[4,5-bis(4-fluorophenyl)-1H-imidazole]

A mixture of 4,5-bis(4-fluorophenyl)-1H-imidazole-2-thione (5.8 g, 0.02 mol) and 1,4-dibromobutane (4.3 g, 0.02 mol) in dioxane (75 ml) was refluxed one hour. After cooling, ether was added and the solid which formed was removed by filtration. This product was air dried and recrystallized from isopropanol to give the title compound as its dihydrobromide salt (hydrate), m.p. 172°–174°.

$C_{34}H_{26}F_4N_4S_2.2$ HBr.$H_2O$ Calculated: 50.38% C; 3.73% H; 6.91% N. Found: 50.30% C; 3.68% H; 6.88% N.

2,2'-[1,4-Butanediylbis(thio)]bis[4,5-bis(4-fluorophenyl)-1H-imidazole dihydrobromide is converted to the title compound by the procedure described in Example 1.

EXAMPLE 8

2,2'-[Methanediylbis(thio)]bis[4,5-bis(4-fluorophenyl)-1H-imidazole]

A mixture of 4,5-bis(4-fluorophenyl)-1H-imidazole-2-thione (8 g, 0.028 mol) and dibromomethane (2.4 g, 0.014 mol) in ethanol (40 ml) was refluxed overnight. The mixture was cooled and the precipitate was removed by filtration. Recrystallization of the solid product from ethanol gave the title compound as its dihydrobromide salt, m.p. 265°.

$C_{36}H_{20}F_4N_4S_2.2$ HBr Calculated: 49.61% C; 2.95% H; 7.47% N. Found: 44.20% C; 3.34% H; 7.68% N.

2,2'-[1,2-Methanediylbis(thio)]bis[4,5-bis(4-fluorophenyl)-1H-imidazole dihydrobromide is converted to the title compound by the procedure described in Example 1.

EXAMPLE 9

2,2'-[1,2-Ethanediylbis(thio)]bis[4,5-bis(3,4-methylenedioxyphenyl)-1H-imidazole]

4,5-Bis(3,4-methylenedioxyphenyl)-1H-imidazole-2-thione was prepared by substitution of an equivalent amount of 4,4'-di(3,4-methylenedioxy)benzoin in either of the procedures for preparing imidazole thiones described in Examples 1 and 2.

A mixture of 4,5-bis(3,4-methylenedioxyphenyl)-1H-imidazole-2-thione (21.5 g, 0.063 mol) and 1,2-dibromoethane (5.9 g, 0.03 mol) in dioxane (400 ml) was refluxed for four hours and then cooled. The precipitate was removed by filtration and recrystallized from methanol to give the title compound as its dihydrobromide salt (hydrate), m.p. 188°–190°.

$C_{36}H_{26}N_4O_8S_2.2HBr.2.5$ $H_2O$ Calculated: 47.32% C; 3.64% H; 6.13% N; 17.49% Br. Found: 47.10% C; 3.58% H; 6.00% N; 17.82% Br.

2,2'-[1,2-Ethanediylbis(thio)]bis[4,5-bis(3,4-methylenedioxy)-1H-imidazole] dihydrobromide is converted to the title compound by the procedure described in Example 1.

EXAMPLE 10

2,2'-[1,3-Propanediylbis(thio)]bis[4,5-bis(4-methoxyphenyl)-1H-imidazole]

A mixture of 4,5-bis(4-methoxyphenyl)-1H-imidazole-2-thione (15.6 g, 0.05 mol) and 1,3-dibromopropane (5 g, 0.025 mol) in ethanol (150 ml) was refluxed for three hours. After cooling, the resulting solid was removed by filtration and discarded. The solvent was removed at reduced pressure to give a yellow foam which was then treated with chloroform-ether. The resulting solid material was removed by filtration, dissolved in chloroform and washed with 10% aqueous sodium hydroxide solution. The solvent was removed at reduced pressure to give the title compound.

The title compound was dissolved in ethanol and 48% hydrobromic acid was added. Ether was added and the salt was collected and recrystallized from ethanol-ether to give the title compound as its dihydrobromide salt (hydrate), m.p. 128°–130°.

$C_{37}H_{36}N_4O_4S_2.2$ HBr.5 $H_2O$ Calculated: 48.48% C; 5.27% H; 6.11% N; 17.44% Br. Found: 48.43% C; 5.15% H; 6.05% N; 18.16% Br.

EXAMPLE 11

2,2'-[1,2-Ethanediylbis(thio)]bis[4,5-bis(4-methylthiophenyl)-1H-imidazole]

4,5-Bis-(4-methylthiophenyl)-1H-imidazole-2-thione, m.p. 296°, was prepared by substitution of an equivalent amount of 4,4'-dimethylthiobenzoin in either of the procedures for preparing imidazole thiones described in Examples 1 and 2.

A mixture of 4,5-bis(4-methylthiophenyl)-1H-imidazole-2-thione (16.2 g, 0.04 mol) and 1,2-dibromoethane (8.8 g, 0.04 mol) in ethanol (250 ml) was refluxed four hours. After cooling, the precipitate was removed by filtration and recrystallized from ethanol to give the title compound, m.p. 237°–238°.

$C_{36}H_{34}N_4S_6$ Calculated: 60.47% C; 4.79% H; 7.84% N. Found: 60.74% C; 5.03% H; 7.77% N.

EXAMPLE 12

2,2'-Thiobis[4,5-bis(4-fluorophenyl)-1H-imidazole

A mixture of 4,5-bis(4-fluorophenyl)-1H-imidazole-2-thione (8.0 g, 0.028 mol), sodium ethoxide (1.9 g, 0.028 mol) and 1,2-diiodotetrafluoroethylene (4.9 g, 0.014 mol) in ethanol (100 ml) was refluxed for two hours and then cooled. The yellow precipitate was collected, washed with ethanol and recrystallized from chloroform to give the title compound, m.p. 234°–236°.

$C_{30}H_{18}F_4N_4S_2$ Calculated: 62.71% C; 3.16% H; 9.75% N. Found: 62.70% C; 3.37% H; 10.00% N.

The title compound was converted to the corresponding dihydrochloride salt by the procedure described in Example 5.

$C_{30}H_{18}F_4N_4S_2.2$ HCl.0.5 $H_2O$ Calculated: 54.88% C; 3.22% H; 8.53% N. Found: 54.62% C; 3.06% H; 8.38% N.

EXAMPLE 13

2,2'-[1,2-Ethanediylbis(sulfonyl)]bis[4,5-bis(4-fluorophenyl)-1H-imidazole]

(A) A mixture of 2,2'-[1,2-ethanediylbis(thio)]bis[4,5-bis(4-fluorophenyl)-1H-imidazole] (3.0 g, 0.005 mol) and 30% hydrogen peroxide (2.8 g, 0.025 mol) in glacial acetic acid (100 ml) was heated at 70° for three hours and then cooled to ambient temperature. The resulting precipitate was filtered, washed with hexane and recrystallized from acetonitrile to give the title compound, m.p. 250°–252°.

$C_{32}H_{22}F_4N_4O_4S_2$ Calculated: 57.48% C; 3.62% H; 8.38% N. Found: 57.70% C; 3.41% H; 8.48% N.

(B) A mixture of 2,2'-[1,2-ethanediylbis(thio)]bis[4,5-bis(4-fluorophenyl-1H-imidazole] (13.4 g, 0.022 mol)

and 30% hydrogen peroxide (12.6 g, 0.112 mol) in glacial acetic acid was stirred above 0° for four hours and then cooled. The precipitate was removed by filtration, washed with hexane and dried in vacuo to give the title compound, m.p. 246°–248°.

EXAMPLE 14

2,2'-[1,2-Ethanediylbis(sulfoxy)]bis[4,5-bis(4-fluorophenyl)-1H-imidazole]

m-Chloroperbenzoic acid (3.5 g, 0.017 mol) was added to a solution of 2,2'-[1,2-ethanediylbis(thio)]bis[4,5-bis(4-fluorophenyl)-1H-imidazole] (5.0 g, 0.008 mol) in glacial acetic acid (500 ml) and the mixture was stirred overnight at ambient temperature. The mixture was filtered and the residue was washed with water, dried in vacuo and recrystallized from dimethylformamide-ethanol to give the title compound, m.p. 175°–180° (dec.).

$C_{32}H_{22}F_4N_4O_2S_2$ Calculated: 60.56% C; 3.49% H; 8.83% N. Found: 60.40% C; 3.62% H; 8.96% N.

The title compound was converted to the corresponding dihydrochloride salt according to the procedure described in Example 5, m.p. 273°–275°.

$C_{32}H_{22}F_4N_4O_2S_2 \cdot 2$ HCl Calculated: 54.32% C; 3.42% H; 7.92% N. Found: 54.62% C; 3.32% H; 8.08% N.

EXAMPLE 15

4,5-Bis(4-fluorophenyl-2-[2-(4,5-bis(4-fluorophenyl)-1H--2-imidazolylthio)ethylthio]-1-methylimidazole A suspension of 2,2'-[1,2-ethanediylbis(thio)]bis[4,5-bis(4-fluorophenyl)-1H-imidazole (6.0 g, 0.01 mol) in N,N-dimethylformamide (50 ml) was treated with sodium hydride (0.48 g, 0.01 mol) under an argon atmosphere. Methyl iodide (1.4 g, 0.01 mol) in N,N-dimethylformamide (10 ml) was added and the mixture was allowed to stir for one hour. The mixture was cooled, filtered and the filtrate was extracted with hexane and poured into water (125 ml). The precipitate was collected, washed with water, dried and chromatographed on a silica gel column with chloroform/ether (gradient) as eluant to give the title compound.

4,5-Bis-(4-fluorophenyl-2-[2-(4,5-bis(4-fluorophenyl)-1H-2-imidazolylthio)ethylthio]-1-methylimidazole (3 g) was dissolved in ethanol and treated with aqueous 48% hydrobromic acid. The salt which precipitated upon addition of ether was recrystallized from isopropanol to give the title compound as its dihydrobromide salt, m.p. 202°–205°.

$C_{33}H_{24}F_4N_4S_2 \cdot 2$ HBr Calculated: 50.91% C; 3.37% H; 7.20% N; 20.53% Br. Found: 50.86% C; 3.34% H; 7.22% N; 20.49% Br.

EXAMPLE 16

2,2'-[1,3-Propan-2-onediylbis(thio)]bis[4,5-bis(4-fluorophenyl-1H-imidazole]

A solution of 4,5-bis(4-fluorophenyl)-1H-imidazole-2-thione (5.8 g, 0.02 mol) and 1,3-dichloropropanone (1.3 g, 0.01 mol) in ethanol (200 ml) was refluxed overnight. The solvent volume was reduced to one half in vacuo and the solution cooled. The resulting precipitate was collected and recrystallized from ethanol to give the title compound as the dihydrochloride salt (hydrate), m.p. 222°–223°.

$C_{33}H_{22}F_4N_4OS_2 \cdot 2$ HCl Calculated: 56.33% C; 3.44% H; 7.96% N. Found: 54.11% C; 3.27% H; 7.52% N.

2,2'-[1,3-Propan-2-onediylbis(thio)]bis[4,5-bis(4-fluorophenyl)-1H-imidazole] dihydrochloride is converted to the title compound by the procedure described in Example 1.

EXAMPLE 17

2,2'-Thiobis[4,5-bis(4-methoxyphenyl)-1H-imidazole]

A mixture of 4,5-bis(4-methoxyphenyl)-1H-imidazole-2-thione (8.0 g, 0.026 mol), 1,2-diiodotetrafluoroethylene (4.5 g, 0.013 mol) and sodium ethoxide (1.74 g, 0.026 mol) in ethanol (100 ml) was refluxed for two hours, then cooled. The precipitate was collected, washed with ethanol and recrystallized from hot acetic acid to give the title compound, m.p. 244°–245°.

$C_{34}H_{30}N_4O_4S$ Calculated: 65.57% C; 4.86% H; 8.90% N. Found: 65.44% C; 4.77% H; 8.66% N.

EXAMPLE 18

2,2'-[1,2-Propanediylbis(thio)]bis[4,5-bis(4-fluorophenyl)-1H-imidazole]

A solution of 4,5-bis(4-fluorophenyl)-1H-imidazole-2-thione (10 g, 0.035 mol) and 1,2-dibromopropane (3.5 g, 0.017 mol) in N,N-dimethylformamide (25 ml) was refluxed for two hours, then cooled. The precipitate was collected, treated with hot chloroform and recrystallized from isopropanol to give the title compound as its dihydrobromide salt, m.p. 243°–245°.

$C_{33}H_{24}F_4N_4S_2 \cdot 2$ HBr Calculated: 50.93% C; 3.37% H; 7.20% N. Found: 50.69% C; 3.39% H; 7.14% N.

2,2'-[1,2-Propanediylbis(thio)]bis[4,5-bis(4-fluorophenyl)-1H-imidazole] dihydrobromide is converted to the title compound by the procedure described in Example 1.

EXAMPLE 19

2,2'-[1,3-Propan-2-oldiylbis(thio)]bis[4,5-bis(4-fluorophenyl)-1H-imidazole]

A solution of 4,5-bis(4-fluorophenyl)-1H-imidazole-2-thione (5.8 g, 0.02 mol) and 1,3-dibromo-2-propanol (2.18 g, 0.01 mol) in ethanol (150 ml) was refluxed for 36 hours. The solvent was removed in vacuo and the yellow residue was dissolved in chloroform. This solution was passed through silica gel which was washed in turn with chloroform, ether and acetone (400 ml each). The residue, after removing the solvent from the acetone fraction, was recrystallized from acetonitrile to give the title compound as its dihydrobromide salt (hydrate), m.p. 219°–221°.

$C_{33}H_{24}F_4N_4OS_2 \cdot 2$ HBr·$H_2O$ Calculated: 48.78% C; 3.47% H; 6.95% N. Found: 48.67% C; 3.34% H; 6.70% N.

2,2'-[1,3-Propan-2-oldiylbis(thio)]bis[4,5-bis(4-fluorophenyl)-1H-imidazole] dihydrobromide is converted to the title compound by the procedure described in Example 1.

EXAMPLE 20

2,2'-Thiobis[4,5-bis(4-trifluoromethylphenyl)-1H-imidazole]

A mixture of 4,5-bis(4-trifluoromethylphenyl)-1H-imidazole-2-thione (3.9 g, 0.01 mol), sodium ethoxide (0.68 g, 0.01 mol) and iodine (1.26 g, 0.005 mol) in ethanol (50 ml) was stirred at ambient temperature for two hours. The resulting precipitate was collected and washed with ethanol and then ether to give the title compound m.p. 343°–345°(dec.).

13

$C_{34}H_{18}F_{12}N_4S_2$ Calculated: 52.72% C; 2.34% H; 7.23% N. Found: 52.61% C; 2.45% H; 7.27% N.

EXAMPLE 21

2,2′-Thiobis[4,5-bis(4-methylthiophenyl)-1H-imidazole]

A mixture of 4,5-bis(4-methylthiophenyl)-1H-imidazole-2-thione (5.2 g, 0.015 mol), sodium ethoxide (1.0 g, 0.015 mol) and iodine (1.9 g, 0.0075 mol) in ethanol (70 ml) was stirred at ambient temperature for three hours. The resulting solid was collected, washed with ethanol and then ether. Recrystallization from N,N-dimethylformamide give the title compound, m.p. 297°-298°.

$C_{34}H_{30}N_4S_6$ Calculated: 59.44% C; 4.40% H; 8.15% N. Found: 59.32% C; 4.30% H; 8.12% N.

EXAMPLE 22

| Ingredients | Amounts |
|---|---|
| 2,2′-[1,2-ethanediylbis(thio)]-bis[4,5-bis(4-fluorophenyl)-1H-imidazole] | 50 mg. |
| magnesium stearate | 5 mg. |
| lactose | 100 mg. |

The above ingredients are screened, mixed and filled into a hard gelatin capsule.

EXAMPLE 23

| Ingredients | Amounts |
|---|---|
| 2,2′-[1,2-ethanediylbis(thio)[-bis[4,5-bis(4-fluorophenyl)-1H-imidazole] | 100 mg. |
| calcium sulfate dihydrate | 150 mg. |
| sucrose | 20 mg. |
| starch | 10 mg. |
| talc | 5 mg. |
| stearic acid | 3 mg. |

The sucrose, calcium sulfate dihydrate and 2,2′-[1,2-ethanediylbis(thio)]bis[4,5-bis(4-fluorophenyl)1H-imidazole] are mixed and granulated with 10% gelatin solution. The wet granules are screened, dried, mixed with the starch, talc and stearic acid, screened and compressed into a tablet.

EXAMPLE 24

| Ingredients | Amounts |
|---|---|
| 2,2′-[1,2-ethanediylbis(thio)-[4,5-bis(4-fluorophenyl)-1H-imidazole] | 50 mg. |
| magnesium stearate | 5 mg. |
| lactose | 75 mg. |

The above ingredients are screened, mixed and filled into a hard gelatin capsule.

Similarly, the other compounds of Formula I may be formulated into pharmaceutical compositions by the procedures of Examples 22-24.

These pharmaceutical compositions are administered orally to a subject in need of regulation of cell-mediated immunity and/or antiarthritic activity within the dose ranges given hereabove.

What is claimed is:

1. A compound of the formula:

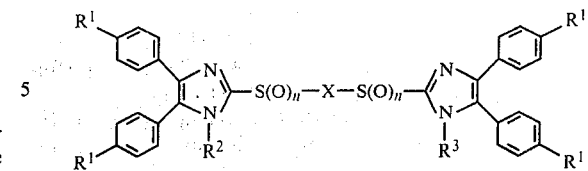

in which:
$R^1$ is methoxy, methylthio, trifluoromethyl, chloro, fluoro, bromo or methylenedioxy when taken with an adjacent position on the phenyl ring;
$R^2$ and $R^3$ are both hydrogen or one is hydrogen and the other is methyl;
n is 0, 1 or 2; and
X is selected from the group consisting of —(CH$_2$)$_m$— where m is 0 to 4 provided that m is not 0 when $R^1$ is chloro,

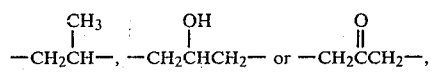

or a non-toxic, pharmaceutically acceptable salt thereof.

2. A compound as claimed in claim 1 where $R^1$ is methoxy or fluoro.

3. A compound as claimed in claim 2 where X is —(CH$_2$)$_m$— and m is 0, 1 or 2.

4. A compound as claimed in claim 2 where X is

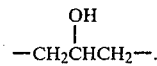

5. A compound as claimed in claim 2 where X is

6. A compound as claimed in claim 3, said compound being 2,2′-[1,2-ethanediylbis(thio)]bis[4,5-bis(4-fluorophenyl)-1H-imidazole].

7. A compound as claimed in claim 3, said compound being 2,2′-thiobis[4,5-bis(4-fluorophenyl)-1H-imidazole].

8. A compound as claimed in claim 3, said compound being 2,2′-[1,2-ethanediylbis(thio)]bis[4,5-bis(4-methoxyphenyl)-1H-imidazole].

9. A compound as claimed in claim 3, said compound being 2,2′-[methanediylbis(thio)]bis[4,5-bis(4-fluorophenyl)-1H-imidazole].

10. A compound as claimed in claim 3, said compound being 2,2′-[1,2-ethanediylbis(sulfoxy)]bis(4,5-bis(4-fluorophenyl)-1H-imidazole].

11. A compound as claimed in claim 3, said compound being 4,5-bis(4-fluorophenyl)-2-[2-(4,5-bis(4-fluorophenyl)-1H-2-imidazolylthio)ethylthio]-1-methylimidazole.

12. A compound as claimed in claim 4, said compound being 2,2′-[1,3-propan-2-oldiylbis(thio)]bis[4,5-bis(4-fluorophenyl)-1H-imidazole].

13. A compound as claimed in claim 5, said compound being 2,2′-[1,3-propan-2-onediylbis(thio)]bis[4,5-bis(4-fluorophenyl-1H-imidazole.

14. A pharmaceutical composition for the regulation of cell-mediated immunity and/or having antiarthritic activity, in dosage unit form, comprising a pharmaceutical carrier and a compound of claim 1.

15. A pharmaceutical composition as claimed in claim 15 in which the compound is 2,2'-[1,2-ethanediylbis(thio)]-bis[4,5-bis(4-fluorophenyl)-1H-imidazole].

16. A method of regulating cell-mediated immunity and/or producing anti-arthritic activity which comprises administering internally to an animal in need thereof a compound of claim 1 in an amount sufficient to produce said activity(ies).

17. A method as claimed in claim 16 in which the compound is 2,2'-[1,2-ethanediylbis(thio)]bis[4,5-bis(4-fluorophenyl)-1H-imidazole].

* * * * *